United States Patent [19]

Drabek et al.

[11] 4,364,959

[45] Dec. 21, 1982

[54] IMINO ETHER SULFIDE DERIVATIVES AND USE AS INSECTICIDES

[75] Inventors: Jozef Drabek, Allschwil, Switzerland; Manfred Böger, Weil am Rhein, Fed. Rep. of Germany

[73] Assignee: Ciba-Geigy Corporation, Ardsley, N.Y.

[21] Appl. No.: 917,447

[22] Filed: Jun. 20, 1978

Related U.S. Application Data

[63] Continuation of Ser. No. 807,107, Jun. 16, 1977.

[51] Int. Cl.³ .................... A01N 35/10; C07C 119/18; C07C 125/06; A01N 37/18
[52] U.S. Cl. ................................. 424/298; 260/453.3; 560/148; 424/300; 424/320; 424/327
[58] Field of Search ........ 260/453 RW, 557 R, 561 S, 260/566 AC, 453.3; 560/148; 424/298, 300, 320, 327

[56] References Cited

U.S. PATENT DOCUMENTS

| | | | |
|---|---|---|---|
| 3,812,174 | 5/1974 | Brown et al. | 424/300 |
| 3,856,972 | 12/1974 | Fujimoto et al. | 424/298 |
| 4,004,031 | 1/1977 | Drabek | 424/327 |
| 4,008,328 | 2/1977 | Siegle et al. | 424/298 |
| 4,072,751 | 2/1978 | D'Silva | 260/561 S |

*Primary Examiner*—Henry R. Jiles
*Assistant Examiner*—Robert C. Whittenbaugh
*Attorney, Agent, or Firm*—Frederick H. Rabin; Harry Falber

[57] ABSTRACT

Compounds of the formula I

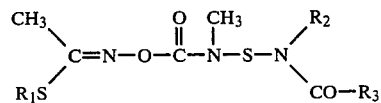

wherein
  $R_1$ is methyl or ethyl,
  $R_2$ is $C_1$–$C_8$-alkyl or $C_3$–$C_8$-cycloalkyl and
  $R_3$ is hydrogen, $C_1$–$C_6$-alkoxy or cyclopropyl possess valuable pesticidal, in particular insecticidal, properties.

13 Claims, No Drawings

IMINO ETHER SULFIDE DERIVATIVES AND USE AS INSECTICIDES

This is a continuation of application Ser. No. 807,107 filed on June 16, 1977.

The present invention relates to novel N,N'-bis-carbamic acid sulphide derivatives which act against pests, to a process for their manufacture and to pesticidal compositions which contain these derivatives as active ingredient, and to a method of controlling pests which comprises the use of the novel compounds.

The N,N'-bis-carbamic acid sulphide derivatives according to the invention have the formula I $$\begin{array}{c} CH_3 \\ \diagdown \\ C=N-O-\overset{O}{\overset{\|}{C}}-\overset{CH_3}{\overset{|}{N}}-S-N\diagup^{R_2} \\ \diagup \\ R_1S \end{array} \quad (I)$$

wherein
R$_1$ represents a methyl or ethyl group,
R$_2$ represents a C$_1$–C$_8$-alkyl or C$_3$–C$_8$-cycloalkyl group and
R$_3$ represents a hydrogen atom or a C$_1$–C$_6$-alkoxy or cyclopropyl group.

Alkyl groups R$_2$ can be branched or straight chain. Possible substituents are for example the methyl, ethyl, n-propyl, isopropyl, n-butyl, sec.-butyl and tert.-butyl group as well as the n-pentyl, n-hexyl and n-octyl group and the isomers thereof. Such groups, up to and including hexyl, also form the alkyl moiety of alkoxy groups represented by R$_3$. By C$_3$–C$_8$-cycloalkyl groups are meant cyclopropyl, cyclopentyl, cyclohexyl, cycloheptyl and cyclooctyl groups.

Particularly preferred compounds on account of their action against pests, especially against insects, are those of the formula I wherein
R$_2$ represents a C$_1$–C$_4$-alkyl, cyclopropyl, cyclohexyl or cyclooctyl group, and
R$_3$ represents a hydrogen atom or a C$_1$–C$_4$-alkoxy or cyclopropyl group.

The compounds of the formula I are obtained by methods which are kown per se, for example by reacting a compound of the formula II $$\begin{array}{c} CH_3 \\ \diagdown \\ C=N-O-\overset{O}{\overset{\|}{C}}-N\diagup^{CH_3} \\ \diagup \\ R_1S \end{array} \quad (II)$$

wherein R$_1$ is as defined in formula (I), in the presence of a base, with a compound of the formula III $$Hal-S-N\diagup^{R_2}_{CO-R_3} \quad (III)$$

wherein R$_2$ and R$_3$ are as defined in formula I and Hal represents a halogen atom, in particular a chlorine or bromine atom.

The process is carried out at a reaction temperature between $-20°$ and $+80°$ C., at normal or elevated pressure and preferably in a solvent or diluent which is inert to the reactants. Suitable solvents or diluents for the reaction are for example: ethers and ethereal compounds, such as diethyl ether, diisopropyl ether, dioxan, dimethoxyethane and tetrahydrofurane; amides, such as N,N-dialkylated carboxamides; aliphatic, aromatic and halogenated hydrocarbons, in particular benzene, toluene, xylenes, methylene chloride, chloroform and chlorobenzene; nitriles, such as acetonitrile; dimethyl sulphoxide; and ketones, such as acetone and methyl ethyl ketone.

Suitable bases are tertiary amines, such as triethylamine, dimethyl aniline, pyridine, picolines and lutidines, and hydroxides, oxides, carbonates and bicarbonates of alkali metals and alkaline earth metals as well as alkalimetalalcoholates, for example potassium tert.butylate and sodium methylate.

The compounds of the formulae II and III used as starting materials are known (see for example U.S. Pat. No. 3,506,698) or they can be prepared in accordance with known methods.

The compounds of the formula I have a broad biocidal action and can be used for controlling a variety of pests, for example as insecticides, acaricides, ectoparasiticides, nematicides and fungicides.

The compounds of the formula I are suitable chiefly for controlling insects. They can thus be used for example for controlling insects of the families Lymantriidae, Noctuidae, Pyralidae, Tineidae, Bruchidae, Chrysomelidae, Curculionidae, Dermestidae, Scarabaedae, Tenebrionidae, Aphididae, Diaspididae, Cimicidae, Pyrrhocoridae, Reduviidae, Agromycidae, Anthomyiidae, Calliphoridae, Culicidae, Muscidae, Stomoxidae, Tipulidae, Trypetidae, Acrididae, Blattidae, Gryllidae and Gryllotalpidae.

The compounds of the formula I are suitable in particular for controlling insects which are injurious to plants (e.g. insects of the genus Spodoptera, Dysdercus, Heliothis, Aphis, Pseudococcus and Chilo) in crops of useful plants and in ornamentals, in particular in crops of rice, cotton, fruit and vegetables.

The insecticidal or acaricidal action can be substantially broadened and adapted to prevailing circumstances by the addition of other insecticides and/or acaricides. Examples of suitable additives are: organic phosphorus compounds, nitrophenols and derivatives thereof, formamidines, ureas, pyethroids, carbamates, and chlorinated hydrocarbons.

The compounds of the formula I may be used as pure active substance or together with suitable carriers and/or additives. Suitable carriers and additives can be solid or liquid and correspond to the substances conventionally used in the art of formulation, for example natural or regenerated substances, solvents, dispersants, wetting agents, tackifiers, thickeners, binders and/or fertilisers.

For application, the compounds of the formula I may be processed to dusts, emulsifiable concentrates, granules, dispersions, sprays, to solutions, or suspensions, in the conventional formulation which is commonly employed in application technology.

The compositions of the present invention are manufactured in known manner by homogeneously mixing and/or grinding active substances of the formula I with the suitable carriers, with or without the addition of dispersants or solvents which are inert to the active substances.

The compounds of the formula I may be processed to the following formulations: Solid formulations:

Dusts, tracking agents and granules (coated granules, impregnated granules and homogeneous granules). Liquid formulations:
 (a) active substances which are dispersable in water: wettable powders, pastes and emulsions;
 (b) solutions.

The content of active substance in the above described compositions is generally between 0.1% and 95%, though higher concentrations can also be used if the compositions are applied from an aircraft or other appropriate application devices.

The compounds(active substances) of the formula I can, for example, be formulated as follows (throughout the present specification all parts and percentages are by weight):

Dusts

The following substances are used to manufacture (a) a 5% and (b) a 2% dust:

(a)

5 parts of active substance,
95 parts of talc;

(b)

2 parts of active substance,
1 part of highly disperse silicic acid,
97 parts of talc.

The active substances are mixed with the carriers and ground.

Granules

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

Wettable powder

The following constituents are used for the preparation of (a) a 40%, (b) and (c) a 25%, and (d) a 10% wettable powder:

(a)

40 parts of active substance,
5 parts of sodium lignin sulphonate,
1 part of sodium dibutylnaphthalenesulpnonate,
54 parts of silicic acid.

(b)

25 parts of active substance,
4.5 parts of calcium lignin sulphonate,
1.9 parts of Champagne chalk/hydroxyethyl cellulose mixture (1:1),
1.5 parts of sodium dibutylnaphthalenesulphonate,
19.5 parts of silicic acid,
19.5 parts of Champagne chalk,
28.1 parts of kaolin, (c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are homogeneously mixed with the additives in suitable mixers and the mixture is then ground in appropriate mills and rollers. Wettable powders are obtained which can be diluted with water to give suspensions of the desired concentration.

Emulsifiable concentrates

The following substances are used to produce (a) a 10%, (b) a 25% , and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethyl formamide,
43.2 parts of xylene;

(b)

25 parts of active substance,
2.5 parts of epoxidised vegetable oil,
10 parts of alkylarylsulphonate/fatty alcohol polyglycol ether mixture,
5 parts of dimethyl formamide,
57.5 parts of xylene;

(c)

50 parts of active substance,
4.2 parts of tributylphenol-polyglycol ether,
5.8 parts of calcium dodecylbenzenesulphonate,
20 parts of cyclohexanone,
20 parts of xylene.

By diluting these concentrates with water it is possible to obtain emulsions of the required concentration.

Spray

The following ingredients are used to prepare (a) a 5% spray, and (b) a 95% spray:

(a)

5 parts of active substance,
1 part of epichlorohydrin,
94 parts of ligroin (boiling range 160°–190° C.);

(b)

95 parts of active substance,
5 parts of epichlorohydrin.

The invention is further illustrated by the following Examples.

EXAMPLE 1

Preparation of N-(N-methylcarbamic acid-1-methylthioethylimide)-N'-(N'-methylcarbamic acid-n-hexyl ester)-sulphide With stirring, 15.8 g of N-chlorosulphenyl-N-methyl-n-hexylurethane and then 6.6 g of pyridine were added dropwise at 5° to 10° C. to a solution of 11.3 g of 1-methylthioethylidenamino-N-methylcarbamate in 70 ml of dichloromethane. The reaction mixture was then stirred for 16 hours at a temperature of 5° to 10° C. The pyridine hydrochloride which had formed was subsequently filtered off by suction, the dichloromethane distilled off, and the crude product chromatographed over silica gel (benzene/methyl acetate), giving the N-(N-methylcarbamic acid-1-methylthioethylimide)-N'-(N'-methylcarbamic acid-n-hexyl ester)-sulphide of the formula

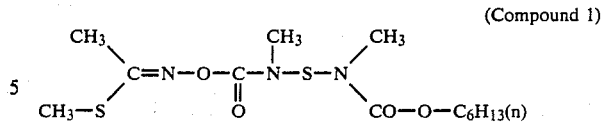

(Compound 1)

with a melting point of 45° C.

The following compounds of the formula I can be obtained in analogous manner:

$$\underset{R_1S}{\overset{CH_3}{\diagdown}}C=N-O-\underset{O}{\overset{O}{\overset{\|}{C}}}-\underset{|}{\overset{CH_3}{N}}-S-N\underset{COR_3}{\overset{R_2}{\diagup}}$$

| Compound | $R_1$ | $R_2$ | $R_3$ | Physical data |
|---|---|---|---|---|
| 2 | $CH_3-$ | $CH_3-$ | cyclopropyl | m.p. 55–59° C. |
| 3 | $CH_3-$ | $CH_3-$ | $CH_3O-$ | $n_D^{20}$: 1.5307 |
| 4 | $CH_3-$ | phenyl | H | $n_D^{20}$: 1.5529 |
| 5 | $CH_3-$ | $(n)C_4H_9-$ | $(n)C_4H_9O-$ | m.p. 62–66° C. |
| 6 | $C_2H_5-$ | $CH_3-$ | $(n)C_6H_{13}O-$ | $n_D^{22}$: 1.5100 |
| 7 | $CH_3-$ | $CH_3-$ | H | $n_D^{20}$: 1.5450 |
| 8 | $C_2H_5-$ | $CH_3-$ | H | $n_D^{20}$: 1.5407 |
| 9 | $CH_3-$ | $(n)C_4H_9$ | $CH_3O-$ | m.p. 90° C. |
| 10 | $C_2H_5-$ | $(n)C_4H_9$ | $CH_3O-$ | $n_D^{20}$: 1.5099 |
| 11 | $C_2H_5-$ | $CH_3-$ | cyclopropyl | m.p. 104–106° C. |
| 12 | $CH_3-$ | cyclooctyl | H | $n_D^{20}$: 1.5534 |
| 13 | $C_2H_5-$ | cyclooctyl | H | $n_D^{20}$: 1.5483 |
| 14 | $CH_3-$ | cyclopropyl | H | m.p. 54–58° C. |
| 15 | $C_2H_5-$ | cyclopropyl | H | $n_D^{20}$: 1.5468 |
| 16 | $CH_3$ | $CH_3$ | $(n)OC_4H_9-$ | m.p. 45–47° C. |
| 17 | $C_2H_5$ | $CH_3$ | $(n)OC_4H_9-$ | $n_D^{20}$: 1.5158 |
| 18 | $CH_3$ | $\underset{(n)C_4H_9}{\overset{C_2H_5}{\diagdown}}CH-CH_2-$ | H | $n_D^{20}$: 1.5218 |
| 19 | $C_2H_5$ | $\underset{(n)C_4H_9}{\overset{C_2H_5}{\diagdown}}CH-CH_2-$ | H | $n_D^{20}$: 1.5183 |

EXAMPLE 2

Insecticidal Stomach Poison Action: *Spodoptera littoralis, Dysdercus fasciatus* and *Heliothis virescens*

Cotton plants were sprayed with an aqueous emulsion containing 0.05% of the compound to be tested (obtained from a 10% emulsifiable concentrate).

After the spray coating had dried, the plants were populated with larvae ($L_3$-stage) of the species *Spodoptera littoralis, Dydercus fasciatus* or *Heliothis virescens*. Two plants were used for each test compound and test species. Evaluation of mortality was made after 2, 4, 24 and 48 hours. The test was carried out at 24° C. and 60% relative humidity.

In this test, the compounds of Example 1 exhibited a very good action against larvae of the species *Spodoptera lottoralis*, *Dysdercus fasciatus* and *Heliothis virescens*.

EXAMPLE 3

Insecticidal Contact Action: *Aphis fabae*

Plants (*Vicia faba*) which have been reared in pots were each populated before the start of the test with approx. 200 aphids of the species *Aphis fabae*. The treated plants were sprayed dripping wet 24 hours later with a solution containing 1000 or 100 ppm of the compound to be tested. Two plants were used for each test compound and test concentration. Evaluation of mortality was made 24 hours later.

In this test, the compounds of Example 1 exhibited a positive action against *Aphis fabae*.

EXAMPLE 4

Insecticidal Contact Action: *Pseudococcus citri*

Plants (*Vicia faba*) which have been reared in pots and cut back to a well-developed pair of leaves, were populated with approx. 200 lice of the species *Pseudococcus citri* 24 hours before the start of the test. The undersides of the leaves populated with lice were then sprayed dripping wet next day with a test solution containing 500 ppm of the compound to be tested. Two plants were used for each test substance and evaluation of mortality was made 24 and 48 hours respectively after the start of the test.

In this test, the compounds of Example 1 acted against *Pseudococcus citri*.

EXAMPLE 5

Insecticidal Action: *Chilo suppressalis*

Rice seedlings of the variety Caloro were reared in plastic pots (6 seedlings per pot) so that their roots became matted to a disc. The roots were then immersed in a solution containing 800, 200 or 100 ppm of the active compound to be tested and allowed to drip off. Then each pot was populated with 5 *Chilo suppressalis* larvae in the $L_2$-stage and the treated plants were subsequently replaced in the pots on top of the larvae.

One plant was used for each test substance and concentration, and evaluation of mortality (in %) was made after 5 days. The test was carried out at 24° C. and 70% relative humidity.

In this test, the compounds of Example 1 exhibited a good action against *Chilo suppressalis*.

What is claimed is:

1. The compound of the formula

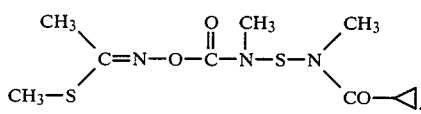

2. The compound of the formula

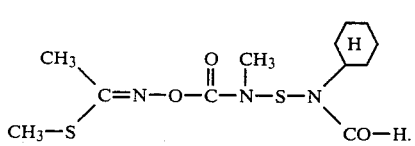

3. The compound of the formula

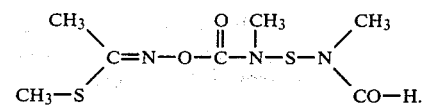

4. The compound of the formula

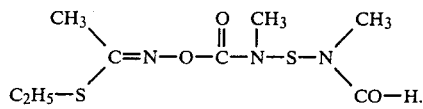

5. The compound of the formula

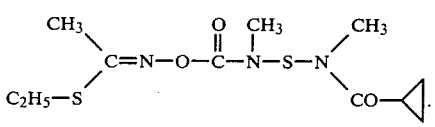

6. The compound of the formula

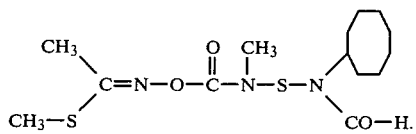

7. The compound of the formula

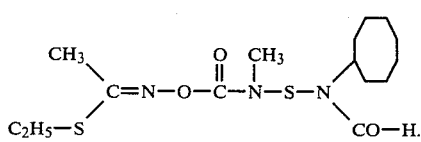

8. The compound of the formula

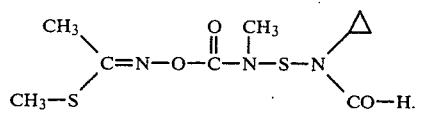

9. The compound of the formula

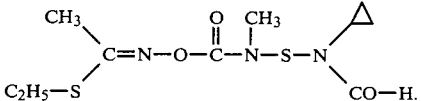

10. The compound of the formula

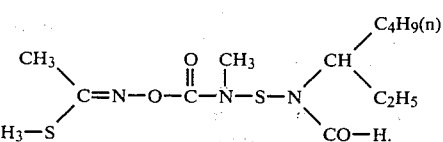

11. The compound of the formula

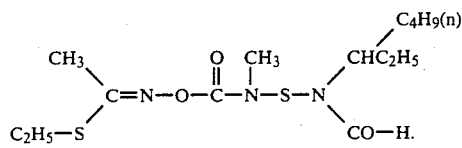
12. An insecticidal composition comprising an insectidially effective amount of a compound of claims 1, 2, 3, 4, 5, 6, 7, 8, 9, 10 or 11, together with an appropriate carrier therefor.
13. A method for controlling insects at a locus, which method comprises applying to said locus an insecticidally effective amount of a compound according to claim 1, 2, 3, 4, 5, 6, 7, 8, 9, 10 or 11.
* * * * *